(12) United States Patent
Song et al.

(10) Patent No.: US 10,130,267 B2
(45) Date of Patent: Nov. 20, 2018

(54) HEART SOUND MONITORING OF PULMONARY HYPERTENSION

(71) Applicant: Medtronic, Inc., Minneapolis, MN (US)

(72) Inventors: Zhendong Song, Medina, MN (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 757 days.

(21) Appl. No.: 13/786,778

(22) Filed: Mar. 6, 2013

(65) Prior Publication Data

US 2013/0237863 A1     Sep. 12, 2013

Related U.S. Application Data

(60) Provisional application No. 61/608,396, filed on Mar. 8, 2012.

(51) Int. Cl.

| A61B 5/0205 | (2006.01) |
| A61M 5/172 | (2006.01) |
| A61N 1/365 | (2006.01) |
| A61B 7/00 | (2006.01) |
| A61B 5/021 | (2006.01) |
| A61B 5/00 | (2006.01) |
| A61B 5/0215 | (2006.01) |
| A61B 5/0456 | (2006.01) |

(52) U.S. Cl.
CPC ............ *A61B 5/0205* (2013.01); *A61B 7/00* (2013.01); *A61B 7/003* (2013.01); *A61M 5/1723* (2013.01); *A61N 1/36585* (2013.01); *A61B 5/021* (2013.01); *A61B 5/0215* (2013.01); *A61B 5/0456* (2013.01); *A61B 5/7285* (2013.01)

(58) Field of Classification Search
USPC ............................................. 607/4
See application file for complete search history.

(56) References Cited

U.S. PATENT DOCUMENTS 4,933,349 A * 6/1990 Irie ................... A61K 31/415
                                                    514/277
5,117,824 A    6/1992 Keimel et al.
(Continued)

FOREIGN PATENT DOCUMENTS

| EP | 1792570 A1 | 6/2007 | |
| WO | WO2011054042 | * 5/2011 | ............ A61M 5/172 |

OTHER PUBLICATIONS

Peacock, A. J. "Primary pulmonary hypertension." (1999) Thorax 54.12: 1107-1118.*

(Continued)

*Primary Examiner* — Jacqueline Cheng
*Assistant Examiner* — Jairo Portillo

(57) ABSTRACT

A medical device system and method that includes sensing a heart sound signal from a first external sensor, determining whether a pulmonary hypertension signature is detected in response to the sensed heart sound signal, sensing a lung sound signal from a second external sensor, determining whether a heart failure signature is detected in response to the sensed lung sound signal, and determining therapy parameters in response to determining whether a pulmonary hypertension signature is detected and determining whether a heart failure signature is detected.

23 Claims, 11 Drawing Sheets

(56) References Cited

U.S. PATENT DOCUMENTS

| | | |
|---|---|---|
| 6,368,283 B1 | 4/2002 | Xu et al. |
| 6,393,316 B1 | 5/2002 | Gillberg et al. |
| 6,527,729 B1 | 3/2003 | Turcott |
| 6,720,473 B1* | 4/2004 | Erf et al. ................ 800/19 |
| 6,869,404 B2 | 3/2005 | Schulhauser et al. |
| 7,828,740 B2 | 11/2010 | Longhini et al. |
| 7,909,772 B2 | 3/2011 | Popov et al. |
| 8,764,674 B2 | 7/2014 | Song et al. |
| 2004/0064056 A1 | 4/2004 | Ogura |
| 2004/0167417 A1* | 8/2004 | Schulhauser et al. ........ 600/513 |
| 2008/0004904 A1* | 1/2008 | Tran ............... A61B 5/0006 705/2 |
| 2008/0091115 A1* | 4/2008 | Popov et al. ................ 600/528 |
| 2008/0091239 A1* | 4/2008 | Johansson et al. ............... 607/4 |
| 2008/0288013 A1 | 11/2008 | Schecter |
| 2009/0062665 A1 | 3/2009 | Peretto et al. |
| 2009/0177262 A1* | 7/2009 | Oberti ............... A61F 2/90 623/1.11 |
| 2009/0299198 A1 | 12/2009 | Carney et al. |
| 2010/0030034 A1* | 2/2010 | Schulhauser et al. ........ 600/301 |
| 2010/0185109 A1 | 7/2010 | Zhang et al. |
| 2010/0331903 A1 | 12/2010 | Zhang et al. |
| 2012/0010095 A1 | 1/2012 | Jones et al. |

OTHER PUBLICATIONS

Nitin Sahgal, "Monitoring and Analysis of Lung Sounds Remotely," International Journal of COPD 2011:6 407-412.
Prosecution History from U.S. Pat. No. 8,764,674, from Oct. 18, 2013 through Feb. 26, 2014, 28 pp.

\* cited by examiner

HEART SOUND MONITORING OF PULMONARY HYPERTENSION

RELATED APPLICATION

The present application claims priority and other benefits from U.S. Provisional Patent Application Ser. No. 61/608,396, filed Mar. 8, 2012, entitled "HEART SOUND MONITORING OF PULMONARY HYPERTENSION" incorporated herein by reference in its entirety.

TECHNICAL FIELD

The disclosure relates to the use of heart sound signals to monitor pulmonary hypertension.

BACKGROUND

A wide variety of medical devices are used for delivering a therapy or monitoring a physiological condition related to a cardiac health within a patient. For example, implantable medical devices, such as cardiac pacemakers or implantable cardioverter defibrillators, provide therapeutic stimulation to the heart by delivering electrical therapy signals, such as pulses for pacing, or shocks for cardioversion or defibrillation. In some cases, such an implantable medical device (IMD) may sense for intrinsic depolarizations of the heart, and control the delivery of such signals to the heart based on the sensing.

In some cases, an IMD device includes sensors for detecting heart sounds signals in addition to electrical signals. As described in Published U.S. Patent Application 2010/0331903 to Zhang et al. entitled "HEART SOUND SENSING TO REDUCE INAPPROPRIATE TACHYARRHYTHMIA THERAPY," incorporated herein by reference in its entirety, heart sounds signals are detected and used to determine whether the heart sounds are normal or abnormal. The heart sounds may also be used to confirm or reject an indication that therapy may be needed based on electrical signals.

Heart failure is a condition affecting thousands of people worldwide. Essentially, congestive heart failure occurs when the heart is unable to pump blood at an adequate rate in response to the filling pressure. A worsening heart failure condition may result in symptoms such as congestion in the tissue, peripheral edema, pulmonary edema, and shortness of breath, and coughing. When heart failure is severe, it can even lead to patient death.

Pulmonary hypertension is abnormally high blood pressure in the arteries of the lungs. The right side of the heart of a patient with pulmonary hypertension must work harder than normal to provide an adequate blood supply to the lungs. In patients with pulmonary hypertension the blood vessels of the lungs have narrowed causing pressure build up. The extra work the heart must do to force the blood through the vessels can result in an enlarging of the right side of the heart. This may eventually result in heart failure in the right side of the heart.

SUMMARY

In general, the disclosure is directed to using heart sounds to monitor for pulmonary hypertension. In some examples, specific heart sounds, along with characteristics of the detected heart sound, are associated with the presence of pulmonary hypertension within a patient.

In one example, the disclosure is directed to a method comprising receiving an A2 heart sound signal from a first external acoustic sensor; receiving a P2 heart sound signal from a second external acoustic sensor; determining at least one A2 heart sound signal parameter from the A2 heart sound signal; determining at least one P2 heart sound signal parameter from the P2 heart sound signal; and based on the at least one P2 heart sound signal parameter, estimating pulmonary arterial pressure.

In another example, the disclosure is directed to a system comprising a telemetry module configured to receive an A2 heart sound signal from a first external acoustic sensor and a P2 heart sound signal from a second external acoustic sensor. The system also comprising a processor configure to determine at least one A2 heart sound signal parameter from the A2 heart sound signal, determine at least one P2 heart sound signal parameter from the P2 heart sound signal, and estimate pulmonary arterial pressure based on the at least one P2 heart sound signal parameter.

In another example, the disclosure is directed to a computer-readable medium containing instructions. The instructions cause a programmable processor to receive an A2 heart sound signal from a first external acoustic sensor; receive a P2 heart sound signal form a second external acoustic sensor; determine at least one A2 heart sound signal parameter form the A2 heart sound signal; determine at least one A2 heart sound signal parameter from the A2 heart sound signal; determine at least one P2 heart sound signal parameter from the P2 heart sound signal; and based on the at least one P2 heart sound signal parameter, estimate pulmonary arterial pressure.

In another example, the disclosure is directed to a system including means for receiving an A2 heart sound signal from a first external acoustic sensor; means for receiving a P2 heart sound signal from a second external acoustic sensor; means for determining at least one A2 heart sound signal parameter from the A2 heart sound signal; means for determining at least one P2 heart sound signal parameter from the P2 heart sound signal; and means for, based on the at least one P2 heart sound signal parameter, estimating pulmonary arterial pressure.

The details of one or more examples consistent with this disclosure are set forth in the accompanying drawings and the description below. Other features, objects, and advantages of the disclosure will be apparent from the description and drawings, and from the claims.

DETAILED DESCRIPTION

As used herein, the term heart sound refers to a feature of a heart sound signal, such as the S1, S2, S3, or S4 heart sounds. There may be multiple heart sounds, e.g., each of an S1, S2, S3 and S4 heart sound, for any given cardiac cycle or heart beat. In some examples, the medical device classifies a heart beat or cardiac cycle as normal or abnormal based on the classifications for one or more heart sounds detected during the heart beat or cardiac cycle. In such examples, the medical device may confirm that a cardiac rhythm is treatable when one or more heart beats are classified as abnormal, or withhold therapy when one or more heart beats are classified as normal.

In general, heart sounds are associated with mechanical vibrations of a patient's heart and the flow of blood through the heart valves, and, thus, are highly correlated with pressure gradients across heart valves and blood pressure. Heart sounds are not only due to vibrations of and pressure within the heart, but may be due to the entire cardiohemic system, e.g., blood, heart, great arteries, etc. Heart sounds recur with each cardiac cycle and are separated and classified according to the activity associated with the vibration. The first heart sound is referred to as "S1," and can be thought of as the vibration sound made by the heart during closure of the atrioventricular (AV) valves, i.e., the mitral valve and tricuspid valve. The S1 sound can sometimes be broken down into the M1 sound, from the closing of the mitral valve, and the T1 sound, from the closing of the tricuspid valve.

The second heart sound is referred to as "S2," and results from the closure of the semilunar valves, i.e., the pulmonary and aortic valves. The S2 heart sound can be thought of as marking the beginning of diastole. The S2 sound can also be broken down into component parts. The P2 sound is from the closing of the pulmonary valve and the A2 sound is from the closing of the aortic valve. The third and fourth heart sounds are referred to as "S3" and "S4," respectively, and can be conceptualized as related to filling of the ventricles during diastole. S3 is due to rapid filling of the ventricles and can occur when the ventricular wall is not relaxed when a large volume of blood flows into the ventricle from the atria. S4 is caused by blood rapidly filling into the ventricles from the atria due to atrial contraction.

In some examples an acoustic sensor may also monitor lung sounds. Collected acoustic waveforms may be analyzed to evaluate respiratory rate, depth of inhalation, and the like, and to determine whether one or more abdominal breath sounds is present. In some examples, the some of the identified lung sounds may be associated with heart failure. For example an IMD or other computing device may determine whether the acoustic waveform indicates the presence of coughing, rales, rhonchi, stridor, or wheezing, as examples.

Figure 2:
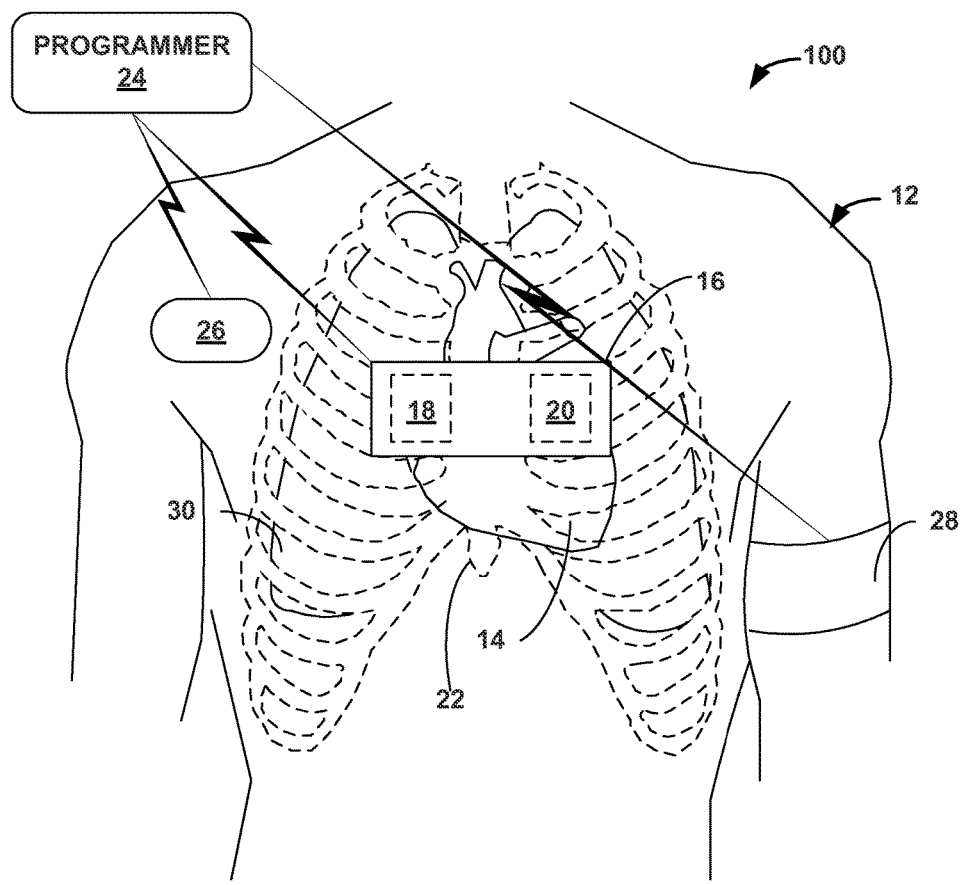
FIG. 2 is a conceptual diagram illustrating another exemplary system that acquires heart sound signals for use in detecting pulmonary hypertension and heart failure in a patient.

Rales are small clicking, bubbling, or rattling sounds in the lungs 30 (FIG. 2). Rales are believed to occur when air opens closed air spaces within the lungs. Rales can be further described as moist, dry, fine, and coarse. Rhonchi are sounds that resemble snoring. Rhonci occur when air is blocked or its passage through large airways of the lungs becomes turbulent. Stridor is a wheeze-like sound heard when a person breathes. Usually stridor is due to a blockage of airflow in the windpipe (trachea) or in the back of the throat. Wheezes are high-pitched sounds produced by narrowed airways. They can be heard when a person exhales.

Pulmonary hypertension is an increase in blood pressure in the pulmonary artery, pulmonary vein, or pulmonary capillaries, together known as the lung vasculature. The increased blood pressure leads to shortness of breath, dizziness, fainting and other symptoms, which are exacerbated by exertion. Pulmonary hypertension may result in a decrease in exercise tolerance and can lead to heart failure. Pulmonary venous hypertension typically presents with shortness of breath while lying flat or sleeping. Pulmonary arterial hypertension, however, is usually not associated with shortness of breath while lying flat.

Consistent with the present disclosure, a correlation between heart and/or lung sounds are used to monitor pulmonary hypertension, including progression and treatment. As discussed in this disclosure, two sensors may be used for detecting the A2 and P2 heart sounds separately. The sensors can be subcutaneous, external, or a combination of both. In some examples, a non-invasive patch sensor may be used to monitor at least heart sounds. The external patch may concurrently monitor both A2 (systemic blood pressure) and P2 (pulmonary blood pressure) heart sounds. The external patch may include at least two sensors, one for monitoring A2 heart sounds and one for monitoring P2 heart sounds. In some examples, the use of an external patch may allow for a patient to be monitored continuously or at regular intervals without the need for invasive procedures to determine pulmonary arterial blood pressure.

In some examples, a patient may be directed to attach, using reusable adhesive, for example, a patch containing acoustic electrodes at a predetermined time of day. Heart sound and/or lung sounds may be collected while the electrodes are in place. In some examples, the A2 and P2 heart sounds may be compared to historic A2 and P2 heart sounds. Changes in one or more characteristics of the heart sound signals may indicate progression of pulmonary hypertension or heart failure. For example, an increase in the P2 heart sound amplitude may indicate an increase in pulmonary pressure.

In some examples, the A2 heart sound may calibrated with a non-invasive blood pressure measurement. In some examples, the relationship between the P2 heart sound and the A2 heart sound may be used to track the progression of, or identify the occurrence of, pulmonary hypertension. For example, if the A2 heart sound indicates that arterial blood pressure is above a certain threshold and the P2 heart sound amplitude is greater than the A2 heart sound, this may indicate that the patient has pulmonary hypertension.

In some examples, the A2 and/or P2 heart sounds may be used to titrate treatment of pulmonary hypertension. In some examples, therapy for treatment of pulmonary hypertension may be adjusted until the P2 heart sound falls below a certain predetermined threshold. The use of external sensors allows for the monitoring of pulmonary pressure without the need for invasive monitoring such as a pressure lead placed in the right ventricle or pulmonary artery. External sensors also allow for monitoring of pulmonary pressure outside of the clinical setting.

After taking proper medication, for example, to treat pulmonary hypertension, the pulmonary vessels should be dilated. In some examples, the sound caused by blood flowing through the dilated blood vessel will be different than the sound resulting from the blood flowing through the constricted vessels of the patient with pulmonary hypertension. In some examples, the sound after vessel dilation will include a higher frequency sound that the constricted vessels. In some examples, monitoring the signal frequency of blood flow may estimate the efficacy of pulmonary hypertension therapy or progression.

In some examples, two acoustic sensors are used. The two acoustic sensors are placed so that one is approximately over the left side of the heart and the other is approximately over the right side of the heart. The use of two acoustic sensors may simplify differentiation between the A2 and P2 heart sounds. In some examples, the two sensors are designed to directionally collect A2 and P2 sounds, one each, concurrently. In some examples, the placement of the two sensors may be based on the results of a patient chest X-ray, or other patient imaging technique, that indicate the aorta and pulmonary artery. One sensor is placed over the aorta while the other is placed over the pulmonary artery. In some examples, each sensor can be designed to confine sound wave detected to the appropriate acoustic waveform. Normal auscultation at either the aortic location or pulmonary location includes sound from both locations because the sound waves from the aortic valve and the pulmonary valve must both travel through the patient's body. In cases where the S2 splice is not obvious, it may be difficult to separate the A2 and P2 heart sounds. However, the use of two specifically designed acoustic sensors, one focused on the aortic value and one focused on the pulmonary valve, provides for greater ease in differentiating between the A2 and P2 heart sounds.

In some examples, heart sounds, in particular the A2 and P2 heart sounds may be used in conjunction with lung sounds and/or other signals such as electrocardiogram (ECG) or impedance signals, to detect heart failure. For examples, when a heart sound signal is used with an ECG signal that is collected by two ECG electrodes, different than the acoustic sensors, the ECG signal can provide information to help identify the S2 heart sound from heart sound signals as well as the interval separating the P2 heart sound and the QRS wave. The interval separating the P2 heart sound and the QRS wave may also suggest the presence of pulmonary hypertension. In some examples, and external acoustic sensor may aid in the monitoring of heart failure progression. In particular, heart sounds may be used to detect pulmonary hypertension induced heart failure progression.

In some examples, timing of heart sound collection may be based on detected lung sounds. For example, A2 and P2 heart sounds may be collected during a phase of no inspiration-expiration to avoid heart sound contamination by respiration sound. In some examples an ECG signal may be used to help determine which portion of the heart sound signal to collect. For example, heart sounds may be collected in a window of time prior to the QRS interval to collect heart sound related to filling. Heart sound may also be collected post QRS interval to collect heart sound related to ejection.

Figure 1:
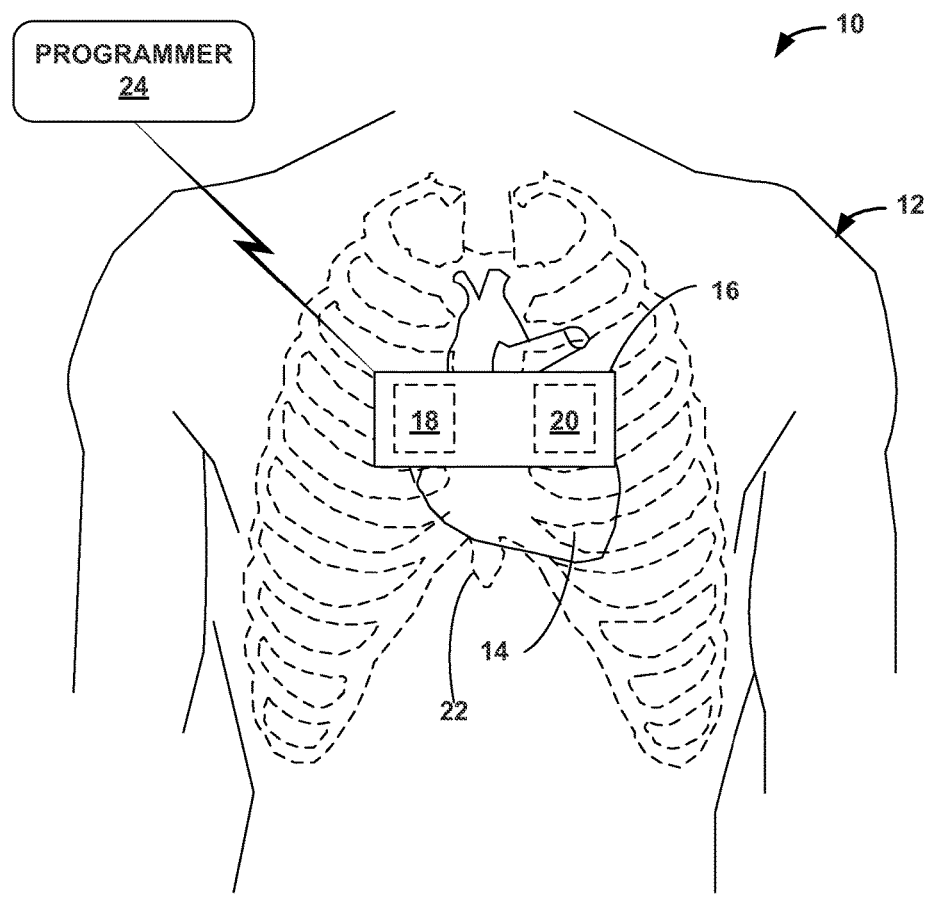
FIG. 1 is a conceptual diagram illustrating an exemplary system that acquires heart sound signals for use in detecting pulmonary hypertension and heart failure in a patient.

FIG. 1 is a conceptual diagram illustrating an exemplary system 10 that detects heart sounds for use in detecting pulmonary hypertension and heart failure in patient 12. In particular, system 10 includes an external patch 16 with acoustic sensors 18 and 20. External patch 16 is placed on patient 12 over sternum 22 so that acoustic sensor 18 is over the right side of the heart 14 and acoustic sensor 20 is over the left side of heart 14. This placement allows for acoustic sensor 18 to better pick up the sound of the aortic valve closing (heart sound A2) and acoustic sensor 20 to better pick up the sound of the pulmonary valve closing (heart sound P2). In some examples, external patch 16 is placed so that acoustic sensors 18 and 20 are located over spaces between the ribs. This also allows for better capture of the heart sounds. In some examples, an optimal location for the two sensors may be determined by referencing a chest X-ray film for the patient.

System 10 also includes a programmer 24. External patch 16 is communicatively coupled to programmer 24. In some examples, programmer 24 takes the form of a handheld computing device, computer workstation, or networked computing device that includes a user interface for presenting information to and receiving input from a user. A user, such as a physician, technician, surgeon, electro-physiologist, or other clinician, may interact with programmer 24 to retrieve physiological or diagnostic information from external patch 16. In certain examples various functions of the programmer 24 may be automated. A user may also interact with programmer 24 to program external patch 16, e.g., select values for operational parameters of the IMD. For example, the operational parameters may be selected automatically in response to one or more acoustic cardiographic metrics. In other examples the function of programmer 24 may be split between an external programmer and an internal programmer within external patch 16.

External patch 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximately to the patient's body near the IMD 16 implant site in order to improve the quality or security of communication between IMD 16 and programmer 24. In other examples, programmer 24 may be located remotely from IMD 16, and communicate with IMD 16 via a network. In some examples, IMD 16 and programmer 24 may work with general network technology and functionality similar to that provided by the Medtronic CareLink® Network developed by Medtronic, Inc., of Minneapolis, Minn.

In some examples, programmer 24 may process heart sound signals received from external patch 16 to determine if a change in patient state has occurred. For example, programmer 24 may determine whether a patient has pulmonary hypertension based on A2 and P2 heart sounds. In some examples, as discussed in more detail below with respect to FIG. 2, programmer 24 may receive one or more additional signals from an implantable medical device or other medical device that monitors other cardiac or lung activity. Programmer 24 may use the heart sounds signals collected by external patch 16 in conjunction with other signals such as lung sound signals to determine whether a patient has pulmonary hypertension induced heart failure.

FIG. 2 is a conceptual diagram illustrating an exemplary system 100 that detects heart sounds for use in detecting pulmonary hypertension and heart failure in patient 12. System 100 include external patch 16, programmer 24, implantable medical device (IMD) 26 and blood pressure monitor 28. In some examples, system 100 may be used to calibrate detected A2 heart sounds with arterial blood pressure detected with blood pressure monitor 28. In addition, system 100 includes an IMD 26 that may be used to provide electrical stimulation therapy to heart 14 of patient 12. In some examples, IMD 26 may be a leadless device. IMD 26 may include a plurality of housing electrodes. The housing electrodes may be formed integrally with an outer surface of a hermetically sealed housing of the IMD, or otherwise be coupled to the housing. The housing electrodes may be defined by uninsulated portions of a portion, e.g., an outward facing portion of the housing of IMD 26. In some examples, the housing of IMD 26 may include an array of electrodes. For example, IMD 26 may include a 4 or 8 electrode array. Programmer 24 may modify therapy parameters for therapy provided by IMD 26 based on heart sounds signals collected by acoustic sensor 18 and 20, on a blood pressure signal from blood pressure monitor 28, or on ECG, ECG, or acoustic signals detected by IMD 26. In other examples, IMD 16 may be a drug pump containing medicines for treatment of pulmonary hypertension or other cardiac disease which may be controlled via close-loop feedback based on A2 and P2 heart sound signals or other signals collected by the system.

Figure 3:
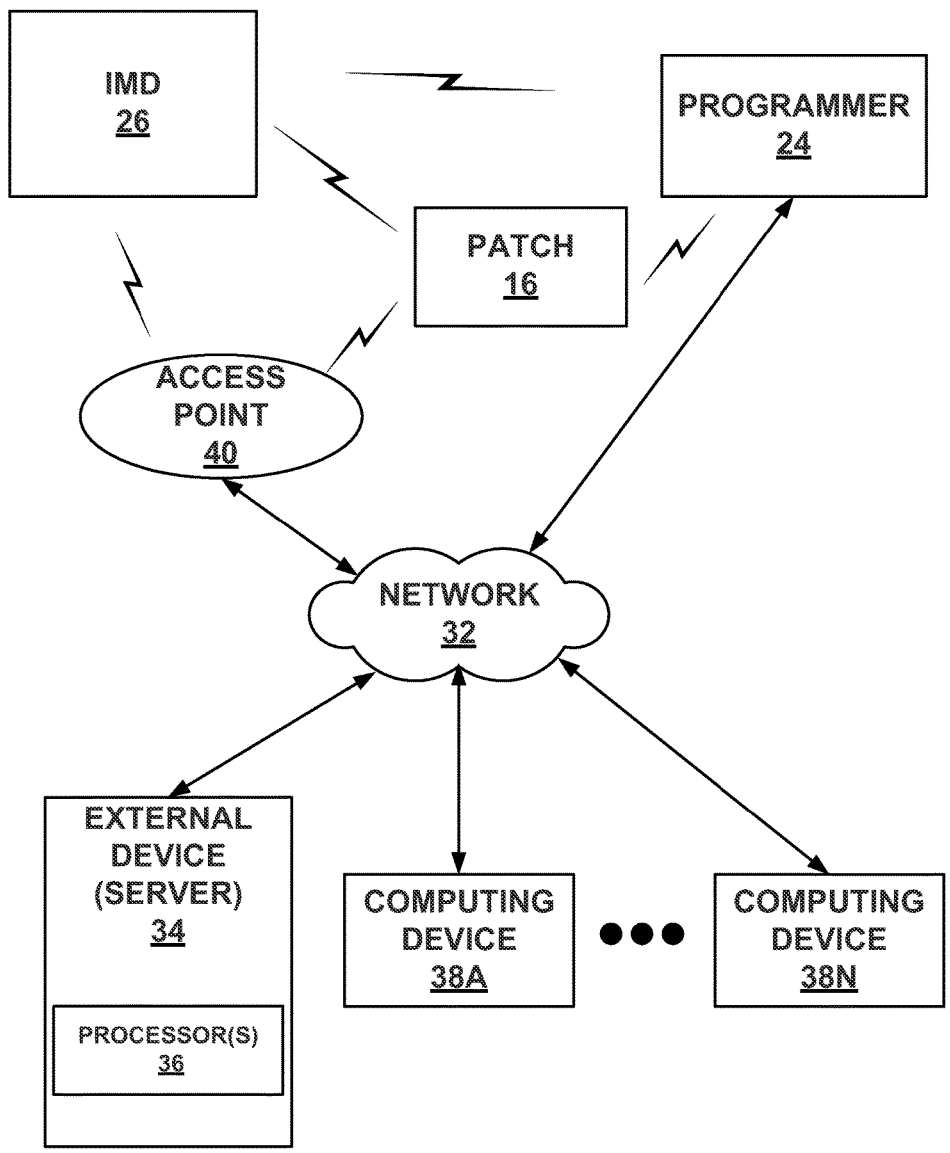
FIG. 3 is a block diagram illustrating an example system that includes an external device, such as server, and one or more computing devices that are coupled to external patch, an IMD and a programmer, as shown in FIG. 2, via a network.

FIG. 3 is a block diagram illustrating an example system that includes an external device, such as server 34, and one or more computing devices 38A-38N that are coupled to external patch 16, IMD 26 and programmer 24 shown in FIG. 2 via a network 32. Network 32 may be generally used to transmit diagnostic information (e.g., an indication of pulmonary hypertension) from programmer 24 to a remote external computing device. In some examples, the heart sounds and/or lung sounds signals may be transmitted to an external device for processing.

In some examples, the information transmitted by external patch 16 and/or IMD 26 may allow a clinician or other healthcare professional to monitor patient 12 remotely. In some examples, external patch 16 may use its telemetry module 52 (discussed in more detail below with respect to FIG. 5) to communicated with programmer 24 via a first wireless connection, and to communicate with an access point 40 via a second wireless connection, e.g., at different times. In the example of FIG. 3, access point 40, programmer 24, IMD 26, server 34, and computing devices 38A-38N are interconnected, and able to communicate with each other, through network 32. In some cases one or more of access point 40, programmer 24, server 34, and computing devices 38A-38N may be coupled to network 32 via one or more wireless connections. External patch 16, IMD 26, programmer 24, server 34 and computing devices 38A-38N may each comprise one or more processors, such as one or more microprocessors, DSPs, ASICs, FPGAs, programmable logic circuitry, or the like, that may perform various functions and operations, such as those described herein.

Access point 40 may comprise a device that connects to network 32 via any of a variety of connections, such as telephone dial-up, digital subscriber line (DSL), or cable modem connections. In other examples, access point 40 may be coupled to network 32 through different forms of connections, including wired or wireless connections. In some examples, access point 40 may be co-located with patient 12 and may comprise one or more programming units and/or computing devices (e.g., one or more monitoring units) that may perform various functions and operations described herein. For example, access point 40 may include a home-monitoring unit that is co-located with patient 12 and that may monitor the activity of external patch 16 and IMD 26. In some examples, server 34 or computing devices 38 may control or perform any of the various functions or operations described herein, e.g., determine, based on heart sounds, whether the patient has pulmonary hypertension.

In some cases, server 34 may be configured to provide a secure storage site for archival of diagnostic information (e.g., occurrence of a pulmonary hypertension and attendant circumstances such as patient posture and activity level) that has been collected and generated from external patch 16, IMD 26 and/or programmer 24. Network 32 may comprise a local area network, wide area network, or global network, such as the Internet. In some cases, programmer 24 or server 34 may assemble pulmonary hypertension and heart failure information in web pages or other documents for viewing by trained professionals, such as clinicians, via viewing terminals associated with computing devices 38. The system of FIG. 3 may be implemented, in some aspects, with general network technology and functionality similar to that provided by the Medtronic CareLink® Network developed by Medtronic, Inc., of Minneapolis, Minn.

In the example of FIG. 3, external server 34 may receive heart sound information from external patch 16 and lung sound information from IMD 26 via network 32. Based on the heart sound information received, processor(s) 36 may preform one or more of the functions described herein with respect to signal analyzer 46 and processor 44 (described with respect to FIG. 4, below). In some examples, cardiac signals including ECG and heart sounds signals are transmitted to an external device and the external device, such as server 34, processes the signals to determine whether a pulmonary hypertension or heart failure has occurred.

Figure 4:
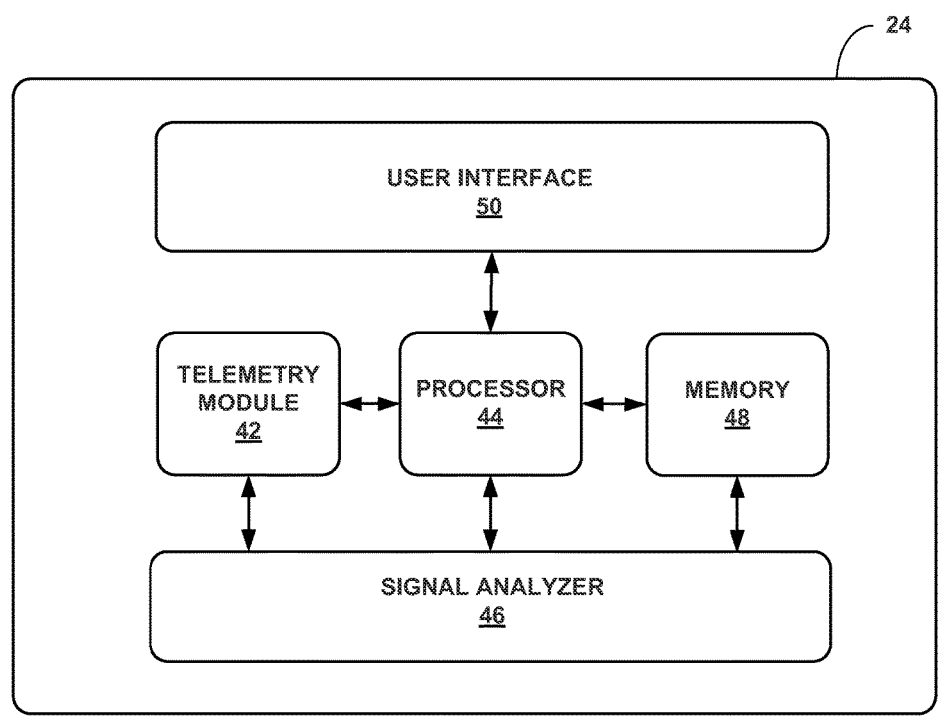
FIG. 4 is a block diagram illustrating an example programmer for programming an external patch and an IMD.

FIG. 4 is a block diagram illustrating an example programmer 24 for programming external patch 16 and IMD 26. Programmer 24 may be provided in the form of a handheld device, portable computer or workstation that provides a user interface to a physician or patient. In the example of FIG. 4, programmer 24 includes processor 44, memory 48, telemetry interface 42, user interface 50, and signal analyzer 46. In general, a user, i.e., a physician or clinician uses programmer 24 to program and control IMD 26. In addition, programmer 24 may be used to determine if patient 12 has developed pulmonary hypertension or heart failure based on information collected by external patch 16 and/or IMD 26.

In the example of FIG. 4, a user interacts with processor 44 via user interface 50 in order access diagnostic and program information regarding patient 12 stored in memory 48. The user may also interact with processor 44 via user interface 50 in order to modify program settings for external patch 16 and/or IMD 26. User interface 50 may be a graphical user interface (GUI). The user interface 50 may also include one or more input media. In put media may include, for example, a keyboard or a touchscreen. In addition, the user interface may include lights, audible alerts, or tactile alerts. Processor 44 may include a microprocessor, a microcontroller, a DSP, an ASIC, an FPGA, or other equivalent discrete or integrated logic circuitry.

In some examples, processor 44 may control external patch 16 and/or IMD 26 via telemetry module 42. For example, processor 44 may be used to determine when external patch 16 collects heart sound signals from acoustic sensors 18 and 20. Processor 44 may also modify one or more therapy parameters used to delivery therapy by IMD 26 in response to heart sound signals collected by external patch 16. In particular, processor 44 may transmit program signal to external patch 16 or IMD 26 via telemetry module 42.

Signal analyzer 46 receives an electrical signal that was generated by acoustic sensor 18 or 20 and transmitted via telemetry module 52 of external patch 16 to telemetry module 42. In one example, signal analyzer 46 may process the sensor signals generated by acoustic sensors 18 and 20 to detect heart sounds. Signal analyzer 46 may also generate one or more acoustic cardiographic metrics indicative of heart performance based on the characteristics of one or more of the detected heart sounds. For example, signal analyzer 46 may determine the amplitude of heart sounds A2 and P2. Signal analyzer 46 may generate an envelope signal and apply an algorithm that uses an adaptively decaying threshold, to detect events within the envelope signal. Signal analyzer 46 extracts event features from the detected events, and determines one or more heart sound parameters based on the features. In some examples, signal analyzer 46 may process the signal from acoustic sensor 18 in order to extract features of heart sound P2 and process the signal from acoustic sensor 20 in order to extract features of heart sound A2.

In some examples, signal analyzer 46 may also process sensor signals for a lung sound sensor 60 in IMD 26. As with the electrical signals from acoustic sensors 18 and 20 of external patch 16, signal analyzer 46 may process the lung sound signal to generate an envelope signal and apply an algorithm that uses an adaptively decaying threshold, to detect events within the envelope signal. Signal analyzer 46 extracts event features from the detected events, and determines one or more lung sound parameters based on the features Signal analyzer 46 may determine if one or more of the lung sound parameters indicate the presence of, or progression of, heart failure within patient 12.

Signal analyzer 46 may provide an indication of a determination of heart failure or pulmonary hyper tension to processor 44. In some examples, signal analyzer 46 may provide an indication of the heart sound signal parameter and the lung sound signal parameters derived from the signals received from external patch 16 and IMD 26. The operation of signal analyzer 46 in accordance with these example methods is described in greater detail with respect to FIGS. 8-10. In any case, a heart and/or lung sound based indication of patient status may be output to processor 44, which may allow, modify or withhold therapy based on patient status. Processor 44 or signal analyzer 46 may store the heart sound signal parameters and lung sound signal parameters in memory 48. In some examples, processor 44 may store the determination of patient status along with any changes made to therapy based on the patient status in memory 48.

Although processor 44 and signal analyzer 46 are illustrated as separate module in FIG. 4, processor 44 and signal analyzer 46 may be incorporated in a single processing unit. Signal analyzer 46 may be a component of or a module executed by processor 44.

Furthermore, the components of and functionality provided by signal analyzer 46 are described herein with respect to examples in which signal analyzer 46 is located within programmer 24. However, it is understood, and discussed in more detail below, that any one or more signal analyzers 46 may be individually or collectively provided by any one or more devices, such as IMD 26, external patch 16, or server 34, to individually or collectively provide the functionality described herein.

Memory 48 includes computer-readable instructions that, when executed by processor 44, cause programmer 24 to perform various functions attributed to programmer 24 and processor 44 herein. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 48 may also store one or more therapy programs or parameters to be executed by IMD 26. Memory 48 may also store instructions regarding when external patch 16 collects heart sound signals.

Telemetry module 42 includes any suitable hardware, firmware, software or any combination thereof for communicating with another device, such as external patch 16 (FIG. 1). Under the control of processor 44, telemetry module 42 may send downlink telemetry to and receive uplink telemetry from external patch 16 and/or IMD 26 with the aid of an antenna, which may be internal and/or external. Information which processor 44 may transmit to IMD 26 via telemetry module 42 may include an indication of a change in disease state of the heart, or a change in programming to change one or more therapy parameters. The indication may be based heart and/or lung sounds.

Figure 5:
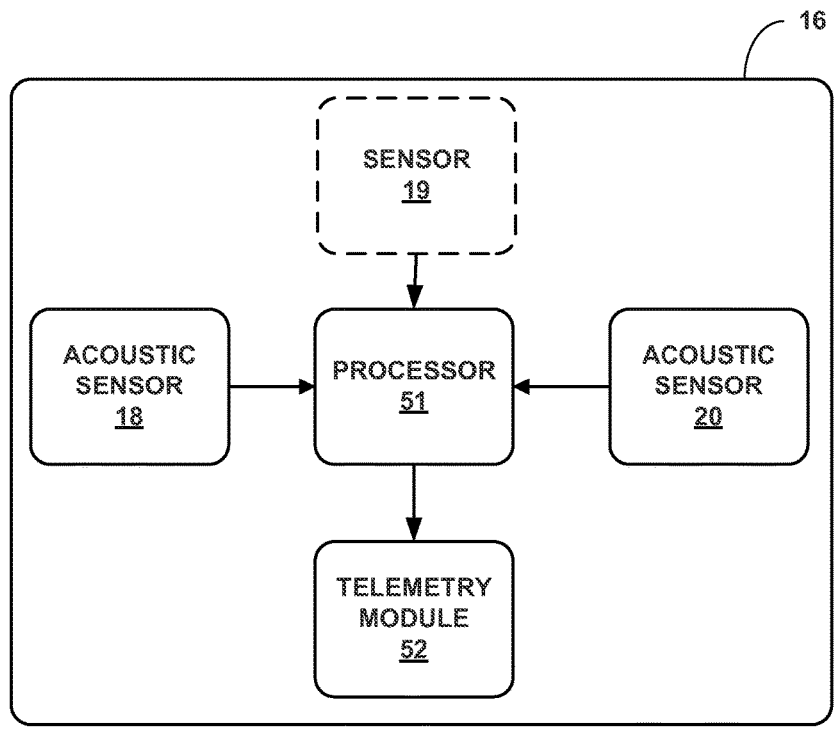
FIG. 5 is a block diagram illustrating an example external patch.

FIG. 5 is a block diagram illustrating an example external patch 16. External patch 16 includes acoustic sensors 18 and 20, processor 51 and telemetry module 52. In some examples, external patch 16 may include one or more additional sensors 19. External patch 16 may also include a power source, not shown. External patch 16 may include a reusable adhesive. The adhesive may be used to hold external patch 16 in place on patient 12 as shown in FIGS. 1 and 2. In some examples, external patch 16 is located on patient 12 so that acoustic sensor 18 is located approximately above the right side of heart 14 and acoustic sensor 20 is located approximately above the left side of heart 14. In certain more specific examples, acoustic sensor 18 is located approximately above the aortic valve of heart 14 and acoustic sensor 20 is located approximately above the pulmonary value of heart 14.

Acoustic sensor 18 generates an electrical signal based on sound or vibration, e.g., sensed heart sounds of patient 12, and may be implemented as a piezoelectric sensor, a microphone, an accelerometer, or other type of acoustical sensor. In some examples, acoustic sensor 18 may comprise one or more sensors. For example, acoustic sensor 18 may include multiple accelerometer devices. Information obtained from acoustic sensor 18 may be used to aid in the detection of pulmonary hypertension and heart failure.

Acoustic sensor 20 also generates an electrical signal based on sound or vibration, e.g., sensed heart sounds of patient 12, and may be implemented as a piezoelectric sensor, a microphone, an accelerometer, or other type of acoustical sensor. In some examples, acoustic sensor 20 may comprise one or more sensors. For example, acoustic sensor 20 may include multiple accelerometer devices. Information obtained from acoustic sensor 20 may be used to aid in the detection of pulmonary hypertension and heart failure.

In some examples, the signals collected by acoustic sensor 18 and acoustic sensor 20 may be filtered at different frequencies. The filtering may be done by processor 51. The location difference between the two sensors may also be used to help differentiate between the A2 and P2 sounds in the collected heart sound signals.

In some examples, acoustic sensors 18 and 20 may detect an acoustic waveform that includes both heart sounds and lung sounds. Processor 51 may amplify the signals from acoustic sensors 18 and 20 prior to transmission via telemetry module 52. In some examples, processor 51 may use band-pass filters to separate heart sound signals from lung sound signals. In some examples, the acoustic waveform may be transmitted to programmer 24 via telemetry module 52 for processing. Processor 44 of programmer 24 may use bandpass filters to separate the heart sound signals from the lung sound signals. In some examples, processor 51 may perform a portion of the signal processing with the other portion of the signal processing performed by processor 44 of programmer 24. For example, processor 51 may separate the heart sound signals from the lung sound signals while processor 44 detects individual heart sounds within the separated heart sound signal.

In some examples, external patch 16 may include one or more additional sensors 19. For example, the sensor 19 may be an electrode configured to detect ECG signals. In other examples, the sensor 19 may be one or more of an additional acoustic sensor, a temperature sensor or an activity level sensor, for example. The signal from sensor 19 may be processed by processor 51 before being transmitted to external programmer 24 or IMD 26 via telemetry module 52.

Figure 6:
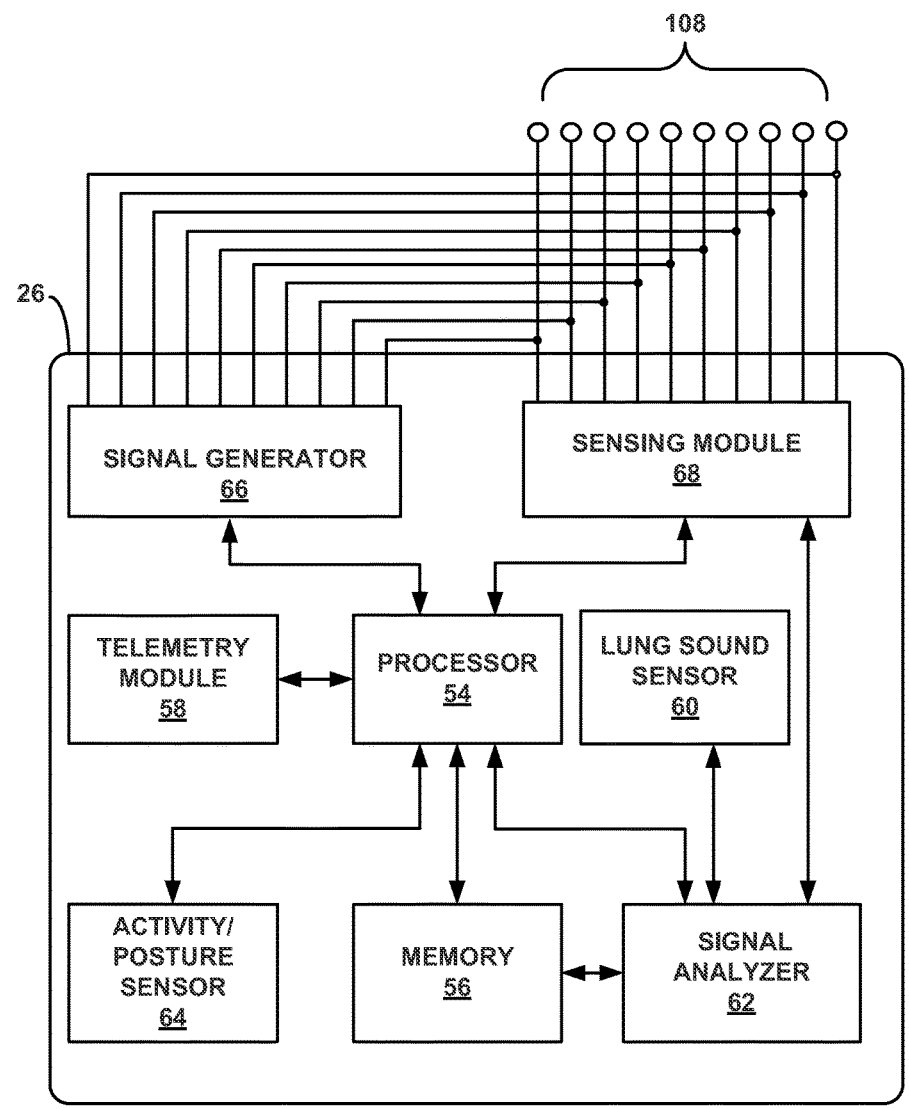
FIG. 6 is a block diagram of an example IMD.

FIG. 6 is a block diagram of an example IMD 26. IMD 26 may include a processor 54, a memory 56, a telemetry module 48, a sound sensor 60, a signal analyzer 62 an activity/posture sensor 64, a signal generator 66 and a sensing module 68. Memory 56 includes computer-readable instructions that, when executed by processor 54, cause IMD 26 and processor 56 to perform various functions attributed to IMD 26 and processor 54 herein. Memory 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 54 may include any one or more of a microprocessor, a controller, a digital signal processor (DSP), an application specific integrated circuit (ASIC), a field-programmable gate array (FPGA), or equivalent discrete or analog logic circuitry. In some examples, processor 54 may include multiple components, such as any combination of one or more microprocessors, one or more controllers, one or more DSPs, one or more ASICs, or one or more FPGAs, as well as other discrete or integrated logic circuitry. The functions attributed to processor 54 herein may be embodied as software, firmware, hardware or any combination thereof. Generally, processor 54 controls signal generator 66 to deliver stimulation therapy to heart 14 of patient 12 according to a selected one or more of therapy programs or parameters, which may be stored in memory 56. As an example, processor 54 may control signal generator 66 to deliver electrical pulses with the amplitudes, pulse widths, frequency, or electrode polarities specified by the selected one or more therapy programs or parameters.

Signal generator 66 is configured to generate and deliver electrical stimulation therapy to patient 12. As shown in FIG. 5, signal generator 66 is electrically coupled to electrodes 108, e.g., via conductors. In some examples, not shown in FIG. 2, IMD 16 may connect to one more leads. In some examples one or more electrodes 108 may be on the housing of IMD 26. For example, signal generator 66 may deliver pacing, defibrillation or cardioversion pulses to heart 14 via at least two of electrodes. In some examples, signal generator 66 delivers stimulation in the form of signals other than pulses such as sine waves, square waves, or other substantially continuous time signals.

Signal generator 66 may include a switch module (not shown) and processor 54 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 68 monitors electrical cardiac signals from any combination of electrode 108. Sensing module 68 may also include a switch module which processor 54 controls to select which of the available electrodes are used to sense the heart activity, depending upon which electrode combination is used in the current sensing configuration.

Sensing module 68 may include one or more detection channels, each of which may comprise an amplifier. The detection channels may be used to sense the cardiac signals. Some detection channels may detect events, such as R-waves or P-waves, and provide indications of the occurrences of such events to processor 54. One or more other detection channels may provide the signals to an analog-to-digital converter, for conversion into a digital signal for processing or analysis by processor 54.

For example, sensing module 68 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 54 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 68 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 68 or processor 54. Processor 54 may analyze the digitized version of signals from the wide band channel. Processor 54 may employ digital signal analysis techniques to characterize the digitized signals from the wide band channel to, for example, detect and classify the patient's heart rhythm. For example, processor 54 may detect the timing of the QRS wave of patient 12.

IMD 26 also includes lung sound sensor 60, signal analyzer 62 and activity sensor 64. Lung sound sensor 60 generates an electrical signal based on sound or vibration, e.g., sensed heart sounds of patient 12, and may be implemented as a piezoelectric sensor, a microphone, an accelerometer, or other type of acoustical sensor. In some examples, lung sound sensor 60 may comprise more than one sensor. For example, lung sound sensor 60 may include multiple accelerometer devices. Activity sensor 64 may also comprise one or more accelerometers. Information obtained from lung sound sensor 60 and activity sensor 64 may be used to provide a risk assessment with regard to worsening heart failure. In some examples, signals from the lung sound sensor 60 and activity sensor 64 are provided to signal analyzer 62 and, based on information extracted from the signals, an assessment of pulmonary hypertension or heart failure may be made.

In the illustrated example of FIG. 6, lung sound sensor 60 is enclosed within the housing of IMD 26. In other examples, lung sound sensor 60 may be located on a lead that is coupled to IMD 26 or may be implemented in a remote sensor that wirelessly communicates with IMD 26.

In any case lung sound sensor 60 is electrically or wirelessly coupled to circuitry contained within IMD 26.

Signal analyzer 62 receives the electrical signal generated by lung sound sensor 60. In one example, signal analyzer 62 may process the sensor signal generated by lung sound sensor 60 to detect lung sounds and respiratory characteristics such as inspiration, expiration, respiratory rate, depth of inspiration, and/or the presence of a cough or other respiratory anomalies such as rales, rhonci, stridor or wheezing. In some examples, signal analyzer 62 may also receive electrical signals generated by acoustic sensors 18 and 20. Signal analyzer 62 may process both the acoustic signals from the acoustic sensors 18 and 20 of external patch 16 and the lung sound sensor 60 of IMD 26. Signal analyzer 62 may process the signals to determine whether pulmonary hypertension or heart failure are present in patient 12 as discussed below with respect to FIGS. 8-10.

Although processor 54 and signal analyzer 62 are illustrated as separate modules in FIG. 6, processor 54 and signal analyzer 62 may be incorporated in a single processing unit. Signal analyzer 62, and any of its components, may be a component of or a module executed by processor 54.

Furthermore, the components of and functionality provided by signal analyzer 62 are described herein with respect to examples in which signal analyzer 62 is located within IMD 26. However, it is understood that any one or more signal analyzers 62 may be individually or collectively provided by any one or more devices, such as IMD 26 and programmer 24, to individually or collectively provide the functionality described herein. Programmer 24 may receive electrical signals generated by lung sound sensor 60 from IMD 26 in examples in which programmer 24 includes signal analyzer 46.

As illustrated in FIG. 6, IMD 26 may also include an activity and/or posture sensor 64. Activity and/or posture sensor 64 may, for example, take the form of one or more accelerometers, or any other sensor known in the art for detecting activity, e.g., body movements or footfalls, or posture. In some examples, activity and/or posture sensor 64 may comprise a three-axis accelerometer. In some examples, lung sound sensor 60 and activity and/or posture sensor 64 may comprise one or more common accelerometers. As will be described in greater detail below with reference to FIGS. 8-10, processor 54 or signal analyzer 62 may use signals from activity and/or posture sensor 64 in various aspects of the heart sound and lung sound analysis. For example, processor 54 may direct acoustic sensors 18 and 20 to collect heart sound signals during periods were the activity level of patient 12 is below a predetermined threshold.

Telemetry module 88 includes any suitable hardware, firmware, software or any combination thereof for communicating with another device, such as programmer 24 or external patch 16 (FIG. 2). Under the control of processor 54, telemetry module 58 may receive downlink telemetry from and send uplink telemetry to programmer 24 with the aid of an antenna, which may be internal and/or external. In some examples, processor 54 may transmit directions to external patch 16 and receive acoustic signals for processing by processor 54 or signal analyzer 63. Processor 54 may also transmit signals, e.g., ECG or ECG signals, produced by sensing module 68 and/or signals by lung sound sensor 60 to programmer 24.

Figure 7:
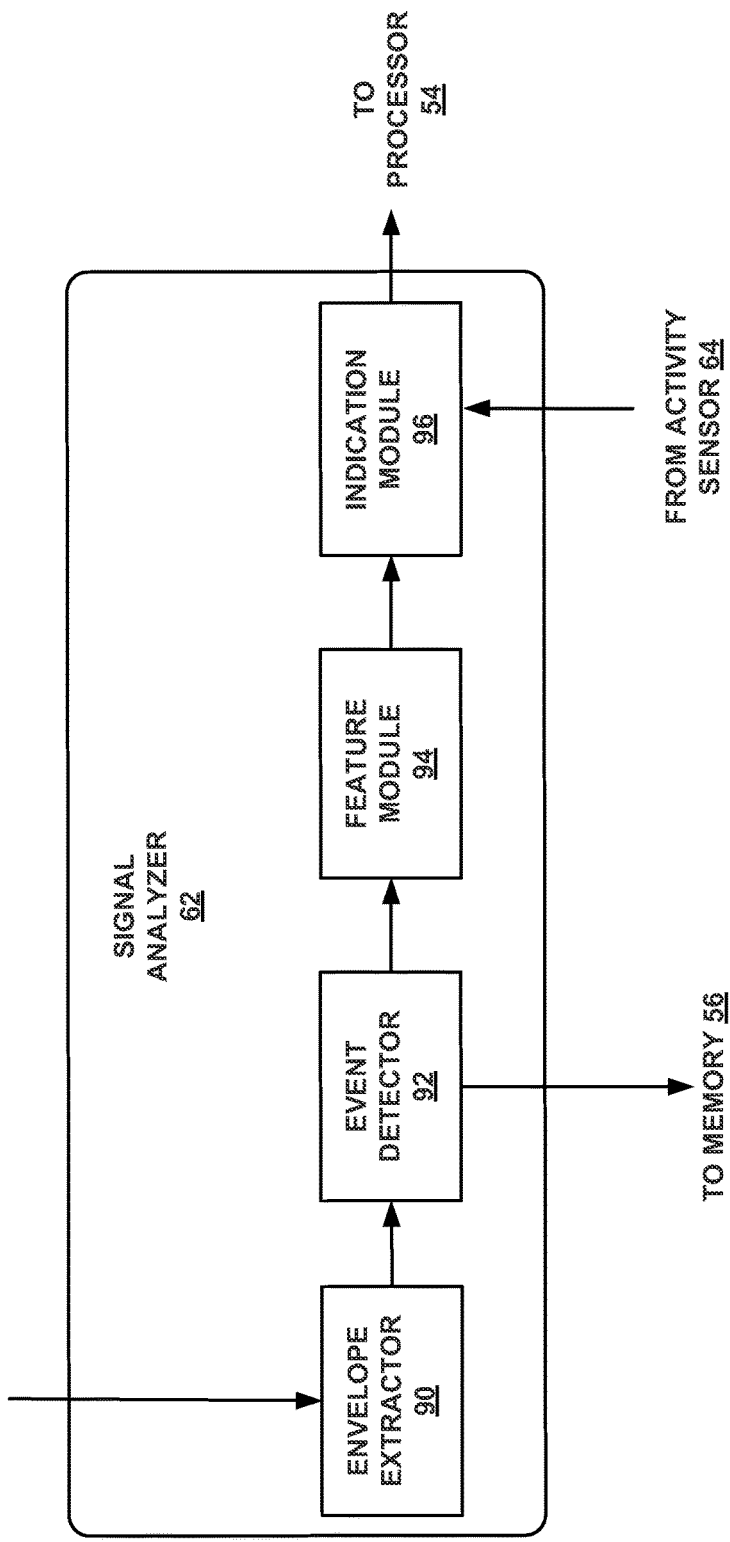
FIG. 7 is a block diagram illustrating an example configuration of signal analyzer.

FIG. 7 is a block diagram illustrating an example configuration of signal analyzer 62. Although described as signal analyzer 62 of IMD 26, signal analyzer 46 functions in a similar manner. As illustrated in FIG. 7, signal analyzer 62 may include an envelope extractor 90, event detector 92, feature module 94, and indication module 96.

Envelope extractor 90 receives one or more electrical signals from acoustic sensors 18 and 20 and/or lung sound sensor 60. Each electrical signal may be digitized and parsed into segments of predetermined length. As an example, the electrical signal generated by lung sound sensor 60 may be sampled at 200 Hertz (Hz) rate and parsed into segments including 100 or more sample points. Generally, envelope extractor 90 processes the received signal to extract an envelope, i.e., generate an envelope signal from the received signal.

In some examples envelope extractor 90 band pass filters, rectifies and smoothes the sensor signal before extracting the envelope signal. For example, envelope extractor 90 may include a high pass filter, e.g., a 40 Hz high pass filter, and a low pass filter, such as a 70 Hz low pass filter, to remove unwanted signal components from the heart sound sensor signal. In some examples a first order infinite impulse response (IIR) high pass filter with a cutoff frequency of 40 Hz and a third order IIR low pass filter with a cutoff of 70 HZ may be used. In some examples a band-pass filter with a 20 Hz high pass filter and a 70 Hz low pass filter is used. In some examples, analog filtering of the heart sound sensor signal may additionally or alternatively be performed prior to digitization of the signal and receipt by envelope extractor 90. As discussed above, IMD 26 may include analog-to-digital conversion circuitry. The filters used for each of the electrical signals from acoustic sensors 18 and 20 and lung sounds sensor 60 may differ. The use of different filters may allow for different information of interest to be extracted from each signal. In some examples, the frequency of the heart sound signal may be separated into different bands by hardware or software filtering. For example, the bands may by 10-100 Hz, 100-1000 Hz, 1000-10,000 Hz, etc. Normal heart sounds have a frequency between 10-200 Hz. In some examples, where disease state is present, the heart sounds may have a frequency above the 10-200 Hz range. For normal heart sounds the frequency of heart sound S1 is lower than heart sound S2. In addition the frequency of respiration rate is much lower (1-5 Hz) than normal heart sounds. This may be helpful in filtering out respiration effects.

In some examples, filtering may be used to detect particular respiratory sounds. For example, in detecting wheezing, a band-pass filter may be used to isolate the sounds resulting from wheezing. Wheezes are generally a continuous sound that can be characterized by both pitch and duration. The dominate frequency of a wheeze may be approximately 400 Hz. Wheezes generally have a duration of greater than 100 milliseconds In addition, both the fundamental and harmonic frequencies are greater than 100 Hz. Rhonchi is a low pitched wheeze with a duration of greater than 100 milliseconds and a frequency of greater than 300 Hz. The dominant frequency in the power spectrum of rhonchi is approximately 100 Hz. Crackles, on the other hand, are generally short and discontinuous sounds with a duration of less than 20 milliseconds. The different characteristics of known respiratory sounds may be used to determine appropriate filtering and detection of abnormal respiratory sounds.

Envelope extractor 90 may also, in some examples, include rectification circuitry and circuitry that sums the rectified signal with left-shifted and right-shifted rectified signals in order to smooth the rectified signal. In this manner, envelope extractor may approximately apply an analytic function transform to the signal for envelope extraction. In some examples, envelope extractor 90 may use other methods to generate the envelope signal, such as the normalized Shannon Energy, true Hilbert transform, or rectifying the derivative of the signal followed by moving window integration of the rectified derivative. In such examples, envelope extractor 90 extracts or generates the envelope signal of the processed signal, i.e., the band pass filtered, rectified, and smoothed signal. Extraction of the envelope signal may further include application of a box-car filter, such as a 16 point box-car filter, to the band pass filtered, rectified, and smoothed signal. Envelope extractor 90 outputs the envelope signal to event detector 92.

Event detector 92 utilizes an algorithm to detect various events within the envelope signal. The event detector 92 may be different for each type of electrical signal received. In some examples the event detector 92 identifies heart sounds as well as lung sounds within each signals envelope to aid in the differentiation between heart sounds and lungs sounds in each signal. Generally, event detector 92 identifies the local maximums of the envelope signal. In order to identify the local maximums, event detector 92 may utilize an adaptively decaying threshold. The adaptively decaying threshold may be determined based on one or more of the running average of detected heart sound and/or cough amplitudes, the running average of the envelope signal amplitude, and the mean heart sound-to-heart sound or cough-to-cough interval. Event detector 92 compares the envelope signal to the adaptively decaying threshold to identify the local maximums. Event detector 92 may store markers, referred to as "event markers," for the identified local maximums within memory 72 or provide the event markers directly to feature module 94. Feature module 94 extracts features of the detected events.

Feature module 94 may process the heart sounds signal in the frequency or time domain. In some examples, feature module 94 may confirm that an event detected by event detector 92 corresponds to the A2 heart sound, the P2 heart sound, or an identifiable lung sound, such as a cough. In some examples, feature module 94 may extract information from the heart sounds signal regarding the characteristics of a cough, for example. In some examples, feature module 94 may both confirm that an event detected by event detector 92 corresponds to a cough and extract information from the heart sounds signal regarding the characteristics of the cough. Similarly, feature module may both confirm that the event detected by event detector 92 corresponds to the A2 heart sound and extract information from the acoustic signal regarding the characteristics of the A2 heart sound. In examples where the feature module 94 extracts features in the frequency domain, feature module 94 may extract features including mean or median frequency, high frequency components, low frequency components, and high/low frequency components energy ratio. In some examples where feature module 94 extracts features of the time domain, feature module 94 may extract information regarding morphology of the A2 or P2 heart sound. Feature module 94 may extract information regarding duration and frequency of lung sound episodes or repetitiveness of coughing sounds episodes. Feature module 94 may also determine the depth a breath or the depth of an abnormal breathing sound such as a cough.

In some examples, various features may be determined based on comparison to a template. In some examples, various features may be determined using template matching schemes that compare detected lung sound anomalies to template lung sound anomalies, such as a wavelet template matching scheme or a "bounded template" matching scheme. An example wavelet template matching scheme is disclosed in U.S. Pat. No. 6,393,316 issued to Jeff Gillberg. An example bounded template matching scheme is disclosed in US Publication No. 20100185109, entitled "A Blurred Template Approach for Arrhythmia Detection," by Xin Zhang, Mark Brown, Xusheng Zhang, and Jeff Gillberg.

In some examples, template lung sound anomalies used for determining various features of the lung sound anomaly such as depth of the breath. In some examples, template anomalies may be lung sounds that were measured during a baseline interval of the patient with no breathing anomaly was present. That is, the template lung sounds may be obtained from patient 12 in an identified or predetermined time period during which the patient is known to have either a period without a lung sound anomaly present or a particular lung anomaly is known to be present. In some examples, memory 72 stores lung sounds signals collected during breathing anomalies having specific characteristics as observed by the patient 12 or a physician.

In some examples, feature module 94 may compare detected A2 or P2 heart sounds to predetermined thresholds or to each other. For example, feature module 94 may compare the amplitude of the P2 heart sound to a stored threshold amplitude associated with a pulmonary pressure indicative of pulmonary hypertension. In some examples, feature module 94 may compare the amplitude of the detected A2 and P2 heart sounds for the same heart beat with each other to determine whether the P2 heart sound amplitude is greater than the A2 heart sound.

In some examples, feature module 94 may load different templates depending upon information from the activity/posture sensor 64. For example, in situations where the activity sensor 64 indicates that the patient 12 is laying down the events may be compared to a different template than when patient 12 when the patient is propped up at an angle, and yet another template when the patient 12 is standing.

Indication module 96 receives information regarding various event features from feature module 94 and an activity signal from activity sensor 64. Based on the information from feature module 94 and activity sensor 64, indication module 96 may generate an indication a patient has pulmonary hypertension, or heart failure.

In some examples, the indication is provided to processor 54. Processor 54 may modify the treatment provided to a patient based on a change inpatient status or heart failure severity. In some examples, processor 54 may provide the indication to programmer 54 so that therapy such as drug therapy may be initiated or changed based on the indication of pulmonary hypertension. In some examples, an indication of pulmonary hypertension may incorporate information from activity sensor 64. For example, an indication of the degree of hypertension may be tempered by a concurrent indication of high activity.

Figure 8:
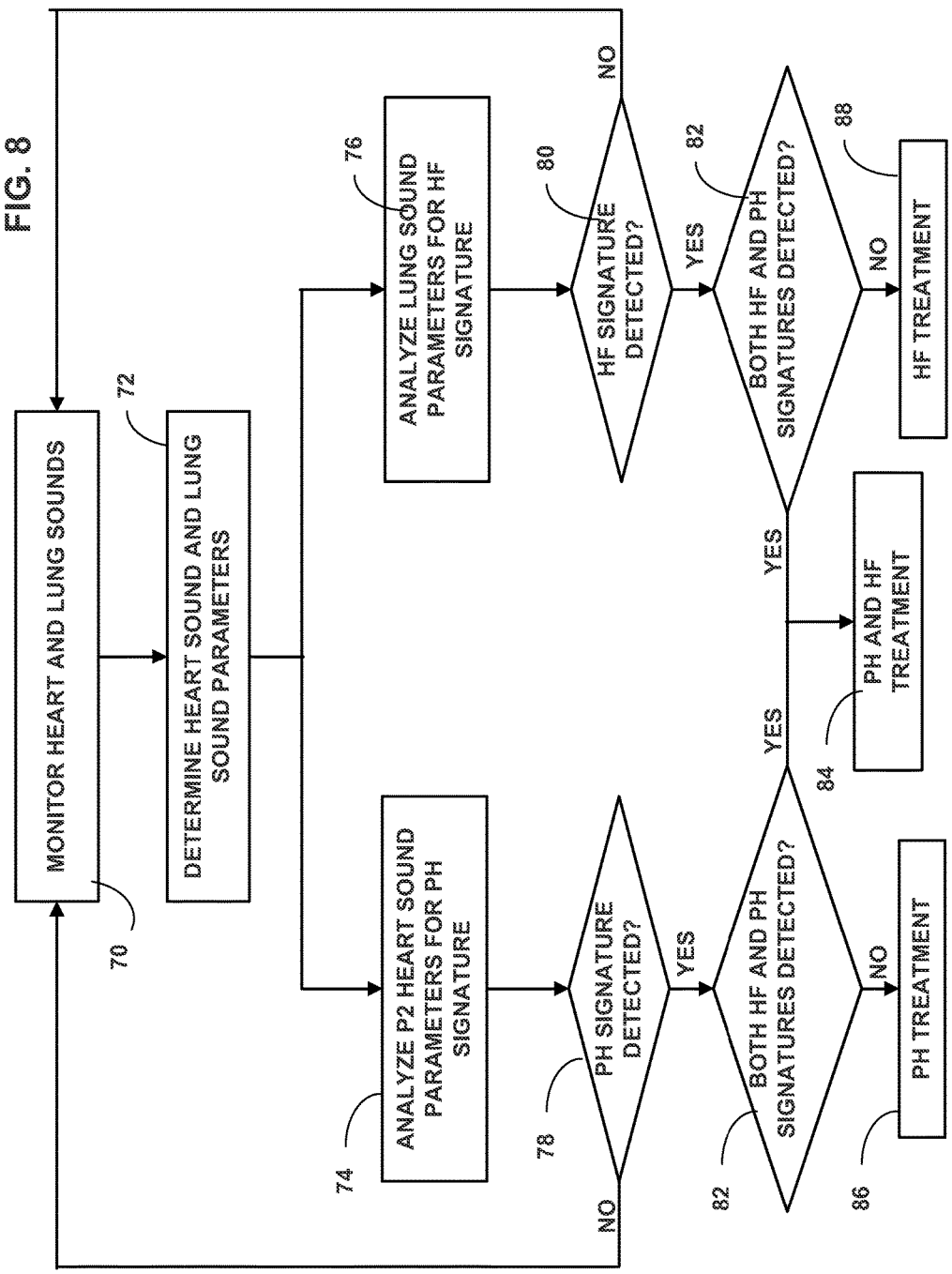
FIG. 8 is a flow chart illustrating an example method consistent with the present disclosure.

FIG. 8 is a flow chart illustrating an example method consistent with the present disclosure. External patch 16 and/IMD 26 monitor heart and lung sounds (70) using acoustic sensors 18 and 20 and/or lung sound sensor 60. In some examples, the acoustic sensor 18 and 20 may be used to monitor both heart sounds and lung sounds. Signal analyzer 46 of programmer 24 or signal analyzer 62 of IMD 26 determine heart sound and lung sound parameters (72). Heart sound parameters may include, for example, heart sounds S1, S2, S3, and S4, length of the split between heart sounds A2 and P2, amplitude of heart sound A2, amplitude of heart sound P2, length of heart sound A2, length of heart sound P2, loudness of the A2 and P2 heart sounds, and the power spectrums of the A2 and P2 heart sounds. Processor 54 analyzes the P2 heart sound parameters for a pulmonary hypertension signature (74). In some examples, the pulmonary hypertension signature may be a P2 sound amplitude above a predetermined threshold. In some examples, the pulmonary hypertension signature may be a P2 sound amplitude that is greater than the A2 sound amplitude. Other pulmonary hypertension signatures may include changes in the interval between A2 and P2, valve regurgitation, heart sound frequency changes, or deviation of the P2 heart sound from a baseline P2 heart sound. In some examples, the heart sound frequency changes may represent valve stiffness. Processor 54 determines if a pulmonary hypertension signature has been detected (78). If no pulmonary hypertension signature has been detected then acoustic sensors 18 and 20 continue to monitor patient heart sounds. Signal analyzer 63 analyzes lung sounds parameters for one or more heart failure signatures (76). In some examples the heart failure signature may be a change in resting respiratory rate. In some examples, the heart failure signature may crackles in the lung sounds or breathlessness. In some examples, the heart failure signature may be based on lung sounds in conjunction with heart sounds and/or an ECG signal. For example the heart failure signature may be in increase in the QRS-S1 interval, a decrease in S1 amplitude, or the appearance of the S3 heart sound. Processor 54 then determines if a heart failure signature has been detected (80). If no heart failure signature is detected, then IMD 26 and/or patch 16 continue to monitor the heart and lung sounds of patient 12.

If a pulmonary hypertension signature is detected (78), processor 54 determines if both a heart failure signature and a pulmonary hypertension signature have been detected (82). If a pulmonary hypertension signature has been detected but a heart failure signature has not been detected processor 54 provides an indication that pulmonary hypertension treatment should begin (86). In some examples, the indication of pulmonary hypertension is provided to programmer 24. Programmer 24 may provide an alert to patient 12 indicating the need to check in with his or her physician regarding treatment of pulmonary hypertension. The physician may in turn start patient 12 on medicine to treat the pulmonary hypertension. In some examples, the indication of pulmonary hypertension may be provided to a drug pump. The drug pump may provide a dose of medication to patient 12 based on the level of pulmonary hypertension present. If both a pulmonary hypertension signature and a heart failure signature are detected, then processor 54 provides an indication that both pulmonary hypertension treatment and heart failure treatment are need. In some examples, the heart failure treatment may include modification to a current cardiac pacing program.

If a heart signature is detected (80), processor 54 determines if both a heart failure signature and a pulmonary hypertension signature have been detected (82). If a heart failure signature is detected but a pulmonary hypertension signature is not detected, then processor 54 provides an indication that heart failure treatment is needed (88). In some examples, the heart failure signature may indicate a change in the severity of a patient's heart failure. The indication may include information regarding how big a change in severity has occurred. Processor 54 may modify one or more parameters of a current treatment program in response to the indication of heart failure. For example, processor 54 may modify one or more parameters of a current cardiac pacing program. In examples where IMD 26 is a drug pump, changes may be made to drug dosage. In other examples, a patient may be placed on oral medication or altered to the need to take a particular medication. Other therapeutic measures taken in response to an indication of heart failure may include neuromodulation. In some examples, the indication of a need for heart failure treatment may be provided to a physician via programmer 24. The physician may manually change one or more treatment parameters. If both a heart failure signature and a pulmonary hypertension signature are detected, then indications of both are produced. Changes in patient treatment may occur in order to treat both pulmonary hypertension and heart failure (84).

Figure 9:
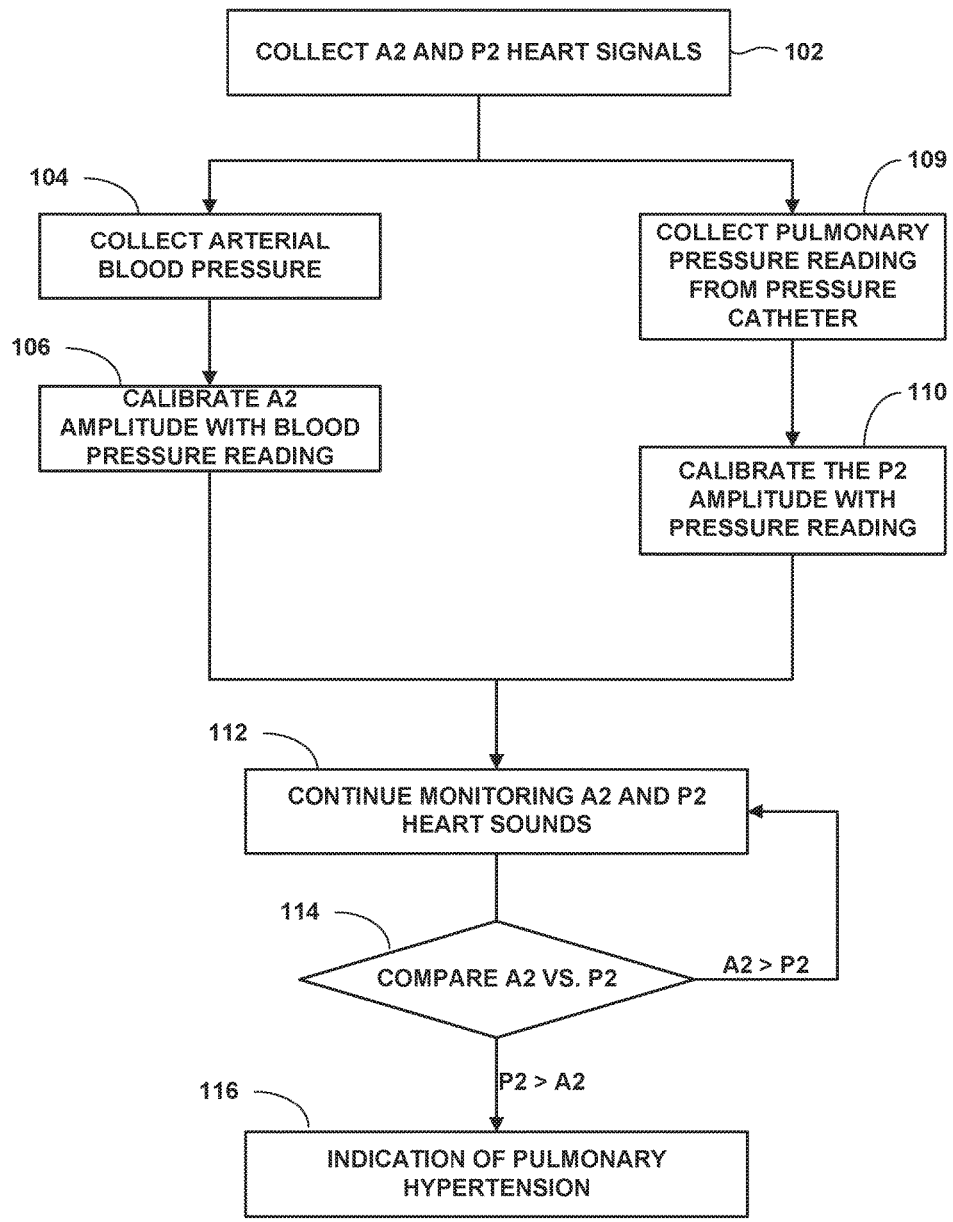
FIG. 9 is a flow chart illustrating another example method consistent with the present disclosure.

FIG. 9 is a flow chart illustrating another example method consistent with the present disclosure. In one example consistent with FIG. 9, acoustic sensors 18 and 20 collect A2 and P2 heart signals (102). As described above, acoustic sensors 18 and 20 may collect heart sounds signals that are then processed by a remote processor such as processor 44 of programmer 24 or processor 54 of IMD 26. In some examples, the acoustic waveform collected by acoustic sensor 20 is filtered and processed to identify the P2 heart sound and the acoustic waveform collected by acoustic sensor 18 is filtered and processed to identify the A2 heart sound. Blood pressure cuff 28 collects an arterial blood pressure (104) reading. The reading may be provided to programmer 24 via wireless link, for example. In some examples, the blood pressure readings using blood pressure cuff 28 may be collected while patient 12 is at the doctor's office. In some examples, patient 12 may have a blood pressure cuff at home and may take blood pressure reading using cuff 28 at predefined intervals. Processor 54 of programmer 24 calibrates the detected A2 heart sound with the blood pressure reading (106). In some examples, calibration occurs over a period of time, or under a variety of conditions. For examples, readings may be taken while a patient is at rest and again while a patient is performing some activity. The collection of different blood pressure and A2 amplitude reading may aid in a more accurate patient specific calibration curve for the relationship between A2 amplitude and arterial blood pressure.

In some examples, a patient may undergo a single invasive procedure to collect a pulmonary pressure reading form a pressure catheter (106). The collection of the pulmonary pressure reading is generally a done under general anesthesia. A catheter is introduced into patient 12 through a large vein such as the internal jugular, subclavian or femoral veins. The catheter is then threaded through the right atrium of heart, the right ventricle, and finally into the pulmonary artery. From the location in the pulmonary artery, the catheter can collect a pulmonary artery pressure reading (109). Processor 44 may calibrate the P2 heart sound amplitude with the collected pulmonary pressure reading (110). The calibration allows for an approximation of current pulmonary pressure to be made based on the P2 heart sound when a pressure catheter is not in place. This in turn, allows for the tacking of a patient's pulmonary pressure with minimal invasion.

After both the A2 heart sounds and the P2 heart sounds have been calibrated, the system, including acoustic sensors 18 and 20, may continue to monitor the A2 and P2 heart sounds (112). Based on the calibration of the A2 and P2 heart sound amplitudes with actual pressure reading, programmer 24 is able to monitor the ongoing pulmonary and arterial blood pressure with minimal invasion. In some examples, processor 44 may compare the A2 amplitude to the P2 amplitude (114). If the amplitude is greater than the P2 amplitude then acoustic sensors 18 and 20 continue to monitor the A2 and P2 heart sounds. If the amplitude of the P2 heart sound is greater than the A2 heart sound, then processor 44 generates an indication of pulmonary hypertension (116).

Figure 10:
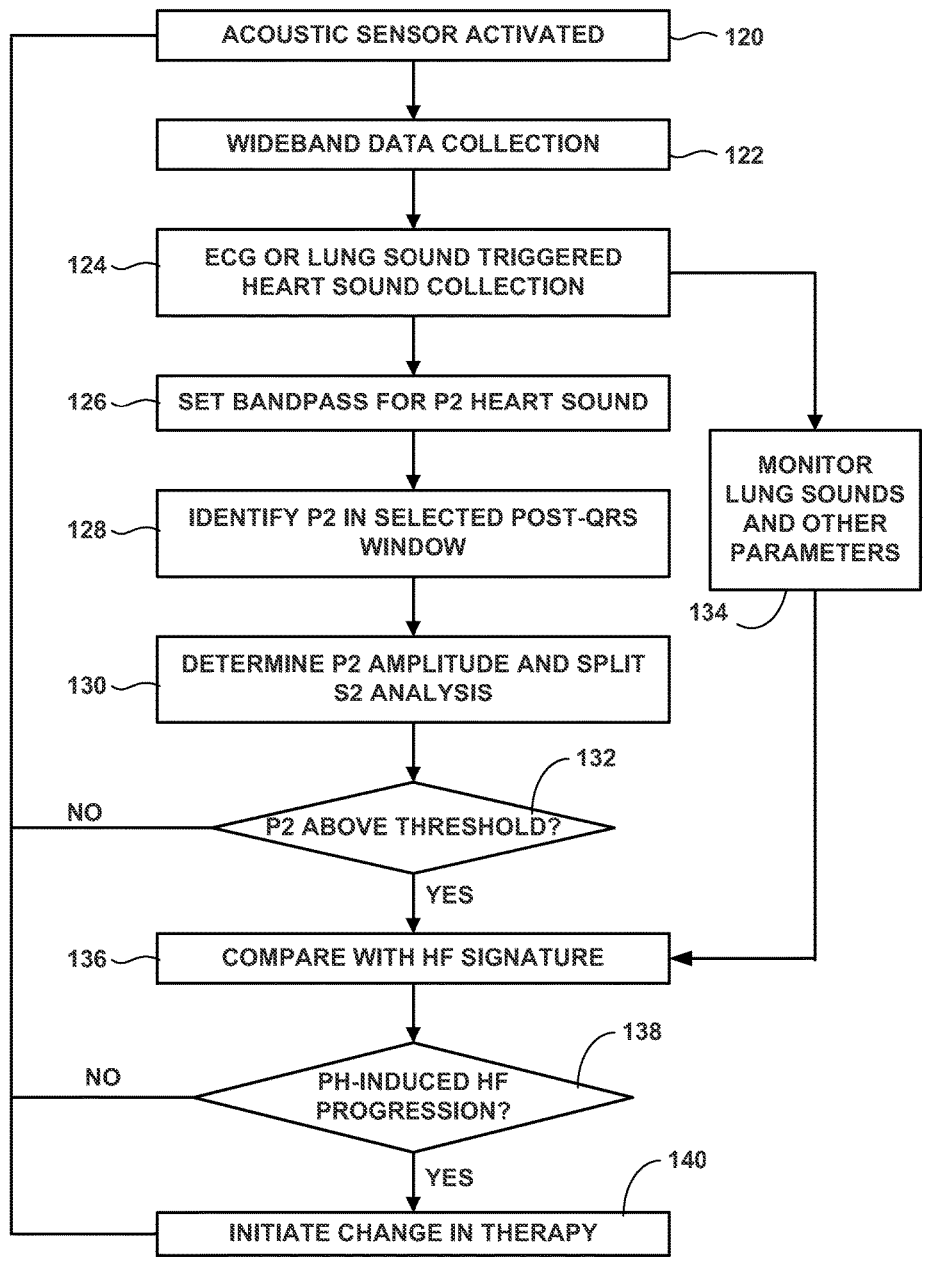
FIG. 10 is a flow chart illustrating another example method consistent with the present disclosure.

FIG. 10 is a flow chart illustrating another example method consistent with the present disclosure. Although this discussed as though implemented by IMD 26 in conjunction with external patch 16, various portions of the method may be performed by other devices, such as programmer 24. In some examples, processor 54 may activate acoustic sensors 18 and 20 (120) based on one or more activation events. For example, acoustic sensors 18 and 20 may be activated at a certain time of day or when patient activity is below a certain level. Acoustic sensors 18 and 20 provide wideband data collection (122). Processor 54 may trigger specific heart sound collection based on ECG or lung sounds (124). For example, activation may also be based whether patient 12 is currently breathing. Heart sounds may also be recorded for short intervals between breaths and following the QRS portion of the ECG signal. Processor 54 or signal analyzer 62 may set a bandpass filter for the P2 heart sound (126). Signal analyzer 62 then identifies the P2 heart sound in a selected post-QRS window (128). For the identified P2 heart sound, signal analyzer 62 then determines P2 amplitude and analyzes the split between A2 and P2 heart sounds in the S2 heart sound (130). Based on the analysis and the determination of the P2 amplitude, and the S2, signal analyzer 62 may determine if the P2 heart sound characteristics are above a predetermined threshold (132). If the P2 heart sound amplitude is not above the threshold then, processor 54 may continue to monitor heart sounds signal via the acoustic sensors. If P2 amplitude is above the threshold (132) then the P2 heart sounds characteristics and outcome of the threshold determination are compared with one or more heart failure signatures (136). The heart failure signatures may be determined based on monitoring of patient lung sounds as well as other heart sound parameters (134), such as the presence of a S3 heart sound. Processor 54 then determines if patient 12 has pulmonary hypertension induce heart failure progression (138). In some examples, processor 54 compares current heart failure signatures to previous heart failure signatures to determine if heart failure within patient 12 has progressed. For example, processor 54 may compare the current amplitude of heart sound S3 to the previous amplitude of heart sound S3. If heart failure has not progressed, IMD 26 may continue to monitor patient heart sounds. If patient 12 has pulmonary hypertension induced heart failure progression (138) then processor 54 initiates a change in therapy (140). Initiation of a change in therapy may include alerting a physician to the change in patient status. In some examples, processor 54 may modify one or more therapy parameters. For example, processor 54 may change one or more pacing parameter. In some examples, processor 54 may reactivate acoustic sensors 18 and 20 and again check for the presence of pulmonary hypertension and/or progression of heart failure in order to determine the efficacy of the changes in therapy.

Figure 11:
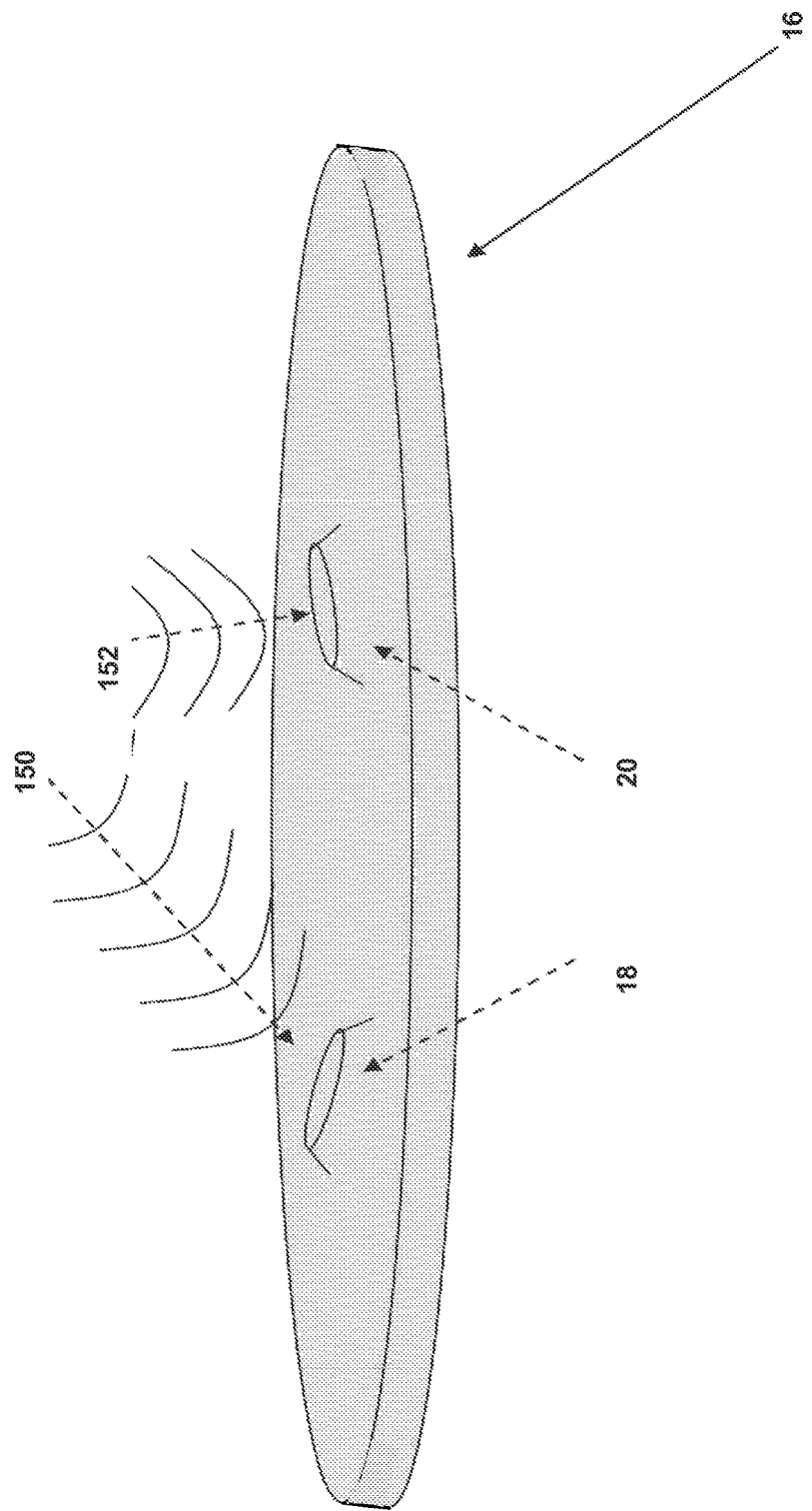
FIG. 11 is a conceptual diagram illustrating an exemplary external patch consistent with the present disclosure.

FIG. 11 is a conceptual diagram illustrating an exemplary external patch consistent with the present disclosure. External patch 16 includes directional acoustic sensor 18 and 20. Directional acoustic sensor 18 may be oriented to pick up sound waves 150 resulting from the aortic valve closure. Directional acoustic sensor 20 may be oriented to pick up sound waves 152 resulting from the pulmonary valve closure. In some examples, the placement of the directional acoustic sensors 18 and 20 may be on a patient chest X-ray, or results of some other imaging technique.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples have been described. These and other examples are within the scope of the following claims.

What we claim is:

1. A method comprising:
analyzing a heart sound signal of a patient for a time interval from a first external sensor to detect a pulmonary hypertension signature;
analyzing a lung sound signal of the patient for the time interval from a second external sensor to detect a heart failure-signature;
when one of the heart failure signature or the pulmonary hypertension signature is detected, then determine whether the other of the heart failure signature or the pulmonary hypertension signature is detected;
delivering a first therapy to the patient via a medical device in response to detecting the pulmonary hypertension signature but not the heart failure signature, the first therapy having a first set of therapy parameters;
delivering a second therapy to the patient via the medical device in response to detecting the heart failure signature but not the pulmonary hypertension signature, the second therapy having a second set of therapy parameters; and
delivering a third therapy to the patient via the medical device in response to detecting both the pulmonary hypertension signature based on the analyzed heart sound signal and the heart failure signature based on the analyzed lung sound signal, the third therapy having a third set of therapy parameters.

2. The method of claim 1, further comprising detecting pulmonary hypertension induced heart failure progression in response to detecting both the pulmonary hypertension signature and the heart failure signature.

3. The method of claim 1, further comprising:
determining an A2 heart sound signal and a P2 heart sound signal in response to the analyzed heart sound signal;
determining at least one P2 heart sound signal parameter from the P2 heart sound signal; and
determining pulmonary arterial pressure in response to the at least one P2 heart sound signal parameter.

4. The method of claim 3, further comprising:
comparing at least one A2 heart sound signal parameter and the at least one P2 heart sound signal parameter; and
determining an indication of pulmonary hypertension in response to the comparing.

5. The method of claim 3, further comprising:
receiving an arterial blood pressure signal from an external blood pressure monitor; and
associating at least one A2 heart sound signal parameter with the arterial blood pressure signal.

6. The method of claim 3, further comprising:
receiving a pulmonary pressure signal from a pressure catheter; and
calibrating the at least one P2 heart sound signal parameter with the pulmonary pressure signal.

7. The method of claim 3, further comprising:
determining whether an amplitude of the P2 heart sound signal is greater than a predetermined threshold;
comparing the P2 heart sound signal and a predetermined heart failure signature; and
determining pulmonary hypertension induced heart failure progression in response to the comparing.

8. The method of claim 7, further comprising analyzing a split between A2 heart sound and a P2 heart sound in an S2 heart sound.

9. The method of claim 1, wherein the first set of therapy parameters are different than the second set of therapy parameters and the third set of therapy parameters, and the second set of therapy parameters are different that the third set of therapy parameters.

10. The method of claim 1, wherein each of the first therapy, the second therapy, and the third therapy comprises at least one of electrical stimulation therapy or drug delivery therapy.

11. A medical device system comprising:
a first external sensor configured to sense a heart sound of a patient;
a second external sensor configured to sense a lung sound signal of the patient;
a medical device including a therapy delivery module configured to delivery therapy to a patient; and
a processor configured to analyze a heart sound signal for a time interval from the first external sensor to detect a pulmonary hypertension signature, analyze a lung sound signal for the time interval from the second external sensor to detect a heart failure signature, when one of the heart failure signature or the pulmonary hypertension signature is detected, then determine whether the other of the heart failure signature or the pulmonary hypertension signature is detected, control delivery of a first therapy to the patient via the medical device in response to detecting the pulmonary hypertension signature but not the heart failure signature, the first therapy having a first set of therapy parameters, control delivery of a second therapy to the patient via the medical device in response to detecting the heart failure signature but not the pulmonary hypertension signature, the second therapy having a second set of therapy parameters; and control delivery of a third therapy to the patient via the medical device in response to detecting both the pulmonary hypertension signature based on the analyzed heart sound signal and the heart failure signature based on the analyzed lung sound signal, the third therapy having a third set of therapy parameters.

12. The medical device system of claim 11, wherein the processor is further configured to detect pulmonary hypertension induced heart failure progression in response to detecting both the pulmonary hypertension signature and heart failure signature.

13. The medical device system of claim 11, wherein the processor is further configured to determine an A2 heart sound signal and a P2 heart sound signal in response to the analyzed heart sound signal, determine at least one P2 heart sound signal parameter from the P2 heart sound signal, and determine pulmonary arterial pressure in response to the at least one P2 heart sound signal parameter.

14. The medical device system of claim 13, wherein the processor is further configured to compare at least one A2 heart sound signal parameter and the at least one P2 heart sound signal parameter, and determine an indication of pulmonary hypertension in response to the comparing.

15. The medical device system of claim 13, further comprising:
an external blood pressure monitor; and
a telemetry module configured to receive an arterial blood pressure signal from the external blood pressure monitor, wherein the processor is further configured to associate at least one A2 heart sound signal parameter with the arterial blood pressure signal.

16. The medical device system of claim 13, further comprising:
a pressure catheter sensing a pulmonary pressure signal; and
a telemetry module configured to receive a pulmonary pressure signal from the pressure catheter, wherein the processor is further configured to calibrate the at least one P2 heart sound signal parameter with the pulmonary pressure signal.

17. The medical device system of claim 13, wherein the processor is further configured to determine whether an amplitude of the P2 heart sound signal is greater than a predetermined threshold, compare the P2 heart sound signal and a predetermined heart failure signature, and determine pulmonary hypertension induced heart failure progression in response to the comparing.

18. The medical device system of claim 17, wherein the processor is further configured to analyze a split between A2 heart sound and a P2 heart sound in an S2 heart sound.

19. The medical device system of claim 11, wherein the first set of therapy parameters are different than the second set of therapy parameters and the third set of therapy parameters, and the second set of therapy parameters are different that the third set of therapy parameters.

20. The medical device system of claim 11, wherein each of the first therapy, the second therapy, and the third therapy comprises at least one of electrical stimulation therapy or drug delivery therapy.

21. A non-transitory computer-readable medium comprising instructions for causing a programmable processor to:
analyze a heart sound signal of a patient for a time interval from a first external sensor to detect a pulmonary hypertension signature;
analyze a lung sound signal of the patient for the time interval from a second external sensor to detect a heart failure signature;
when one of the heart failure signature or the pulmonary hypertension signature is detected, then determine whether the other of the heart failure signature or the pulmonary hypertension signature is detected;
control delivery of a first therapy to the patient via a medical device in response to detecting the pulmonary hypertension Signature but not the heart failure signature, the first therapy having a first set of therapy parameters;

control delivery of a second therapy to the patient via the medical device in response to detecting the heart failure signature but not the pulmonary hypertension signature, the second therapy having a second set of therapy parameters; and control delivery of a third therapy to the patient via the medical device in response to detecting both the pulmonary hypertension signature based on the analyzed heart sound signal and the heart failure signature based on the analyzed lung sound signal, the third therapy having a third set of therapy parameters.

22. A medical device system comprising:

a first external sensor configured to sense a heart sound of a patient;

a second external sensor configured to sense a lung sound signal of the patient;

a medical device including a therapy delivery module configured to delivery therapy to a patient;

a processor configured to analyze a heart sound signal for a time interval from the first external sensor to detect a pulmonary hypertension signature, analyze a lung sound signal for the time interval from the second external sensor to detect a heart failure signature, when one of the heart failure signature or the pulmonary hypertension signature is detected, then determine whether the other of the heart failure signature or the pulmonary hypertension signature is detected, control delivery of a first therapy to the patient via the medical device in response to detecting the pulmonary hypertension signature but not detecting the heart failure signature, the first therapy having a first set of therapy parameters; control delivery of a second therapy to the patient via the medical device in response to detecting the heart failure signature but not the pulmonary hypertension signature, the second therapy having a second set of therapy parameters; and control delivery of a third therapy to the patient via the medical device in response to detecting both the pulmonary hypertension signature based on the analyzed heart sound signal and the heart failure signature based on the analyzed lung sound signal:, the third therapy having a third set of therapy parameters; and an external programmer device including a graphical user interface configured to display an indicator of at least one of the analyzed lung sound, the analyzed heart sound, the detection of the pulmonary hypertension signature but not the heart failure signal, the detection of the heart failure signature but not the pulmonary hypertension signature, or the detection of both the pulmonary hypertension signature and the heart failure signature.

23. A method comprising:

analyzing a heart sound signal of a patient from a first external sensor to detect a pulmonary hypertension signature and separately analyzing a lung sound signal of the patient from a second external sensor to detect a heart failure signature;

determining that one of the heart failure signature or the pulmonary hypertension signature is detected;

determining, in response to the determination that the one of the heart failure signature or the pulmonary hypertension signature is detected, whether the other of the heart failure signature or the pulmonary hypertension signature is detected;

delivering a first therapy to the patient via a medical device in response to detecting the pulmonary hypertension signature but not the heart failure signature, the first therapy having a first set of therapy parameters;

delivering a second therapy to the patient via the medical device in response to detecting the heart failure signature but not the pulmonary hypertension signature, the second therapy having a second set of therapy parameters; and delivering a third therapy to the patient via the medical device in response to detecting both the pulmonary hypertension signature based on the analyzed heart sound signal and the heart failure signature based on the analyzed lung sound signal, the third therapy having a third set of therapy parameters.

* * * * *